(12) United States Patent
Yee et al.

(10) Patent No.: US 11,086,049 B2
(45) Date of Patent: *Aug. 10, 2021

(54) ANTI-MICROBIAL BANDAGE CONTACT LENS WITH OCULAR DRUG DELIVERY

(71) Applicant: The Regents of the University of California, Oakland, CA (US)

(72) Inventors: Albert Yee, Irvine, CA (US); Rachel Rosenzweig, Irvine, CA (US); Mary Nora Dickson, Newport Beach, CA (US); Elena Liang, Irvine, CA (US); Szu-Wen Wang, Irvine, CA (US); Sara Heedy, Oakland, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/150,976

(22) Filed: Oct. 3, 2018

(65) Prior Publication Data
US 2019/0101669 A1    Apr. 4, 2019

Related U.S. Application Data

(60) Provisional application No. 62/567,675, filed on Oct. 3, 2017.

(51) Int. Cl.
*A61L 27/20* (2006.01)
*G02B 1/04* (2006.01)
(Continued)

(52) U.S. Cl.
CPC ............ *G02B 1/043* (2013.01); *A61K 9/0051* (2013.01); *A61L 27/20* (2013.01); *A61L 27/222* (2013.01);
(Continued)

(58) Field of Classification Search
CPC ......... G02B 1/043; G02C 7/049; A61L 27/52; A61L 2400/12; A61L 2430/16
See application file for complete search history.

(56) References Cited

U.S. PATENT DOCUMENTS 6,106,552 A    8/2000   Lacombe et al.
10,828,394 B2  11/2020  Yee et al.
(Continued)

FOREIGN PATENT DOCUMENTS

WO    2013172794 A1    11/2013
WO    2015055656 A1     4/2015
(Continued)

OTHER PUBLICATIONS

Zhang et al, "Surface modification of polymethyl methacrylate intraocular lenses by plasma for improvement of antithrombogenicity and transmittance", Applied Surface Science 225, pp. 6840-6845, 2009.*

(Continued)

*Primary Examiner* — Lakshmi S Channavajjala
(74) *Attorney, Agent, or Firm* — KPPB LLP

(57) ABSTRACT

The technology relates to a prophylactic bandage contact lens that prevents microbial infections in an eye as well as treats infection by dispensing antimicrobial medication at controlled rates. In one embodiment, the invention provides a bandage with nanostructures, and provides a continuous treatment over 10 days and shields the eye from the environment, significantly diminishing the risk of infection while allowing damaged tissues to heal.

24 Claims, 2 Drawing Sheets

(51) Int. Cl.
| | |
|---|---|
| *A61K 9/00* | (2006.01) |
| *A61L 27/54* | (2006.01) |
| *A61L 27/52* | (2006.01) |
| *A61L 27/22* | (2006.01) |
| *G02C 7/04* | (2006.01) |
| *A61L 31/16* | (2006.01) |

(52) U.S. Cl.
CPC ............... *A61L 27/52* (2013.01); *A61L 27/54* (2013.01); *A61L 31/16* (2013.01); *A61L 2300/404* (2013.01); *A61L 2300/406* (2013.01); *A61L 2300/408* (2013.01); *A61L 2400/12* (2013.01); *A61L 2430/16* (2013.01); *G02C 7/049* (2013.01)

(56) References Cited

U.S. PATENT DOCUMENTS

| | | | | | |
|---|---|---|---|---|---|
| 2003/0175325 | A1* | 9/2003 | Chatelier | ................ | A61L 27/34 424/429 |
| 2007/0168025 | A1 | 7/2007 | Darougar et al. | | |
| 2007/0227428 | A1 | 10/2007 | Brennan et al. | | |
| 2008/0317982 | A1 | 12/2008 | Hecht et al. | | |
| 2009/0194913 | A1 | 8/2009 | Chang et al. | | |
| 2009/0266418 | A1 | 10/2009 | Hu et al. | | |
| 2010/0036488 | A1 | 2/2010 | de Juan, Jr. et al. | | |
| 2010/0239637 | A1* | 9/2010 | Ciolino | .................... | G02C 7/04 424/429 |
| 2011/0125260 | A1 | 5/2011 | Shen | | |
| 2011/0135814 | A1 | 6/2011 | Miyauchi et al. | | |
| 2011/0160851 | A1 | 6/2011 | Mueller-lierheim | | |
| 2012/0040461 | A1 | 2/2012 | Beachley et al. | | |
| 2013/0059113 | A1* | 3/2013 | Hatton | .................... | B08B 17/06 428/116 |
| 2013/0244889 | A1 | 9/2013 | Yim et al. | | |
| 2014/0305904 | A1 | 10/2014 | Lan | | |
| 2015/0104522 | A1 | 4/2015 | Xu | | |
| 2015/0104622 | A1 | 4/2015 | Chong et al. | | |
| 2015/0273755 | A1 | 10/2015 | Yee et al. | | |
| 2017/0293158 | A1* | 10/2017 | Markus | ............ | B29D 11/00134 |
| 2019/0075789 | A1 | 3/2019 | Yee et al. | | |
| 2019/0076573 | A1* | 3/2019 | Yee | .......................... | A61L 29/14 |
| 2020/0163753 | A1 | 5/2020 | Yee et al. | | |

FOREIGN PATENT DOCUMENTS

| | | |
|---|---|---|
| WO | 2017156460 A1 | 9/2017 |
| WO | 2017160658 A1 | 9/2017 |
| WO | 2017156460 A8 | 5/2018 |

OTHER PUBLICATIONS

International Preliminary Report on Patentability for International Application PCT/US2017/021908, Report dated Sep. 11, 2018, dated Sep. 20, 2018, 9 Pgs.

International Preliminary Report on Patentability for International Application PCT/US2017/021926, Report dated Sep. 18, 2018, dated Sep. 27, 2018, 7 Pgs.

International Search Report and Written Opinion for International Application No. PCT/US2017/021908, Search completed Jun. 23, 2017, dated Jul. 7, 2017, 12 Pgs.

International Search Report and Written Opinion for International Application No. PCT/US2017/021926, Search completed Apr. 25, 2017, dated Jun. 1, 2017, 8 Pgs.

Banerjee et al., "Antifouling Coatings: Recent Developments in the Design of Surfaces That Prevent Fouling by Proteins, Bacteria, and Marine Organisms.", Advanced Materials, Feb. 11, 2011, vol. 23 Issue 6, pp. 690-718.

Chung et al., "Impact of engineered surface microtopography on biofilm formation of *Staphylococcus aureus*", Biointerphases, Jun. 2007, vol. 2, Issue 2, pp. 89-94.

Hasan et al., "Selective bactericidal activity of nanopatterned superhydrophobic cicada *Psaltoda claripennis* wing surfaces", Appl Microbiol Biotechnol, 2013, vol. 97, pp. 9257-9262.

Ivanova et al., "Natural Bactericidal Surfaces: Mechanical Rupture of Pseudomonas aeruginosa Cells by Cicada Wings", Small, Aug. 20, 2012, vol. 8, Issue16, pp. 2489-2494.

Kirschner et al., "Bio-Inspired Antifouling Strategies, Annual Review of Materials Research", 2012, vol. 42, pp. 211-229.

Kopplmayr et al., "Nanoimprint Lithography on curved surfaces prepared by fused deposition modelling", Surface Topography: Metrology and Properties. Jun. 2015, vol. 3, No. 2, 024003, 12 pgs.

Liu et al., "Bio-Inspired Design of Multiscale Structures for Function Integration, Nano Today", Apr. 2011, vol. 6 issue 2, pp. 155-175.

Pogodin et al., "Biophysical Model of Bacterial Cell Interactions with Nanopatterned Cicada Wing Surfaces", Biophysical Journal vol. 104, Issue 4, 2013 pp. 835-840.

Sun et al., "Wetting properties on nanostructured surfaces of cicada wings", The Journal of Experimental Biology Oct. 1, 2009, vol. 212, Issue 19, pp. 3148-3155.

Yao et al., "Atomic Force Microscopy and Theoretical Considerations of Surface Properties and Turgor Pressures of Bacteria", Colloids and Surfaces B: Biointerfaces 2002, vol. 23, pp. 213-230.

Zhang et al., "Cicada Wings: A Stamp from Nature for Nanoimprint Lithography", Small Dec. 2006, vol. 2 Issue 12, pp. 1440-1443.

Deodhar et al., "Conserved Activity of Reassociated Homotetrameric Protein Subunits Released from Mesoporous Silica Nanoparticles", Langmuir, 2018, Published Dec. 12, 2017, vol. 34, pp. 228-233,. doi: 10.1021/acs.langmuir.7b03310.

Farrand et al., "Prevalence of Diagnosed Dry Eye Disease in the United States Among Adults Aged 18 Years and Older", American Journal of Ophthalmology, Jun. 30, 2017, vol. 182, pp. 90-98, doi: 10.1016/j.ajo.2017.06.033.

Gause et al., "Mechanistic modeling of ophthalmic drug delivery to the anterior chamber by eye drops and contact lenses", Advances in Colloid and Interface Science, 2016, Available Online Aug. 14, 2015, vol. 233, pp. 139-154;. doi: 10.1016/j.cis.2015.08.002.

Tang et al., "Mesoporous Silica Nanoparticles: Synthesis, Biocompatibility and Drug Delivery", Advanced Materials, Feb. 29, 2012, vol. 24, No. 12, pp. 1504-1534, doi: 10.1002/adma.201104763.

* cited by examiner

ANTI-MICROBIAL BANDAGE CONTACT LENS WITH OCULAR DRUG DELIVERY

CROSS-REFERENCE TO RELATED APPLICATIONS

The present application claims the benefit of priority under 35 U.S.C. § 119(e) of provisional application Ser. No. 62/567,675, filed Oct. 3, 2017, the contents of which are hereby incorporated by reference.

FIELD OF THE INVENTION

The present disclosure is in the medical and biomedical field, specifically ocular medical devices.

BACKGROUND OF THE DISCLOSURE

Contact lenses are the second most used medical device, with more than 30 million wearers in the U.S. Contact lenses commonly become infected by bacteria and fungi, leading to one million doctor and hospital visits annually, at a cost of $175 million to the U.S. healthcare system (Collier S A, et al., MMWR Morb Mortal Wkly Rep. 2014). Symptoms of such detrimental infections include eye pain, redness, light sensitivity, blurred vision, excessive tearing and discharge, often leading to blindness. Current treatment consists of applying drug-containing eye drops, which are minimally effective because only a small percentage of the drug is delivered; the rest is washed away by natural tears. Moreover, the therapeutic effect generally lasts for less than an hour. There is an unmet need for a drug delivery device that can act over a much longer term and that would not significantly impede vision of the patient. A prophylactic bandaged contact lens (BCL) for clinical applications against resistant bacterial and fungal infections provides a solution for infection prevention, treatment, and overall quality of life.

Since the 1960s, researchers have explored hydrogel BCLs for ocular protection after injury to promote healing with a variety of topical pharmaceutical agents. However, no such device incorporates antimicrobial materials and nanotextures for the prevention of fungal infection. Thus, there is a need in the art for novel and more effective ocular medical devices and devices related to contact lenses.

SUMMARY OF THE INVENTION

Various embodiments include an eye lens, comprising an inner surface layer with an antimicrobial shielding, a core layer, and an outer surface layer. In another embodiment, the outer surface layer comprises antimicrobial shielding. In another embodiment, the antimicrobial shielding comprises antimicrobial nanopillars. In another embodiment, the antimicrobial shielding comprises antimicrobial chitosan. In another embodiment, the antimicrobial shielding comprises antimicrobial nanoarchitectures. In another embodiment, the core layer is drug eluting. In another embodiment, the core layer comprises a hydrogel composite. In another embodiment, the core layer provides a continuous and/or constant rate of drug release. In another embodiment, the core layer releases drugs natamycin, voriconazole, and/or erythromycin. In another embodiment, the eye lens is transparent. In another embodiment, the core layer comprises chitosan and/or gelatin matrix. In another embodiment, the core layer is reinforced by chitin nanofibers for mechanical stability. In another embodiment, the core layer provides strength, stability, shape, and/or release of drugs from the lens. In another embodiment, the inner surface layer comprises a lubricating hydrogel. In another embodiment, the outer surface layer comprises a lubricating hydrogel with antimicrobial nanopillars. In another embodiment, the inner surface layer and outer surface layer provides wearability and/or antimicrobial shielding for the eye lens. In another embodiment, the inner surface layer and outer surface layer comprises PMMA antimicrobial nanoarchitectures.

Other embodiments include a device, comprising an antimicrobial bandage contact lens (BCL), wherein the antimicrobial BCL shields the eye from the environment while providing continuous long term treatment. In another embodiment, the antimicrobial BCL acts as a prophylactic device that prevents microbial infections in an eye using inherently antimicrobial biomaterials with nanotopography. In another embodiment, the antimicrobial BCL treats existing infection by dispensing antimicrobial medication at controlled rates over a period of up to 10 days. In another embodiment, the antimicrobial BCL is transparent. In another embodiment, the antimicrobial BCL diminishes the risk of infection while simultaneously allowing damaged tissues to heal. In another embodiment, the device allows the user to maintain vision to the extent allowed by the nature of the injury. In another embodiment, the antimicrobial BCL comprises a plurality of nanostructures fabricated on the surface.

Other embodiments include a method of treating an eye condition in an individual, comprising providing an eye lens comprising an inner surface layer with an antimicrobial shielding, a core layer, and an outer surface layer, and treating the eye condition in the individual by applying the eye lens to an injured eye of the individual. In another embodiment, the eye condition is an eye infection. In another embodiment, the eye lens is transparent. In another embodiment, the individual wears the eye lens over a therapeutically effective period of several days. In another embodiment, the outer surface layer comprises antimicrobial nanopillars. In another embodiment, the core layer comprises a drug eluting hydrogel composite. In another embodiment, the individual wears the eye lens over a period of about 10 days. In another embodiment, the eye condition is a physically injured eye.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

The core layer is fabricated from a biocomposite which both provide mechanical strength and functions as an antifungal and antibacterial drug reservoir. Insert: Atomic force microscopy (AFM) image of (top) nanopillared structures demonstrated on poly(methyl methacrylate) (PMMA), and (bottom) chitin nanofibers embedded in a gelatin matrix. Scale bars are 500 nm.

Figure 3:
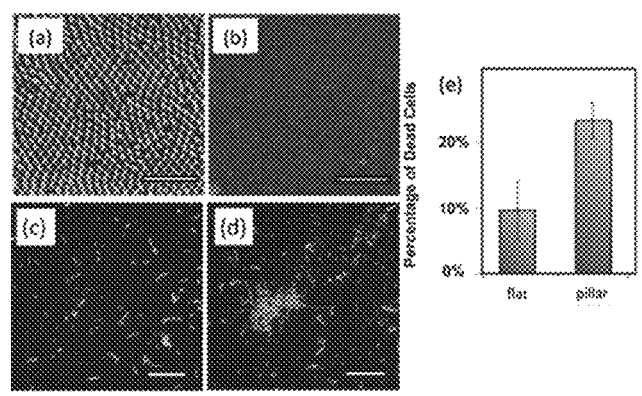

FIG. 3 illustrates, in accordance with embodiments herein, (a) Scanning electron microscopy (SEM) image of uniform 100 nm diameter PMMA nanopillars on imprinted surface. (b) SEM image of flat PMMA surface. (c-d) Fluorescence microscopy images of live (green) and dead (red) *Escherichia coli* bacteria on (c) nanopillars (d) on flat surface. Increased numbers of live bacterial cells is observed on flat surfaces. (e) Increase in percentage of dead cells measured on nanopillared surface. Scale bars are 1 µm.

Figure 4:
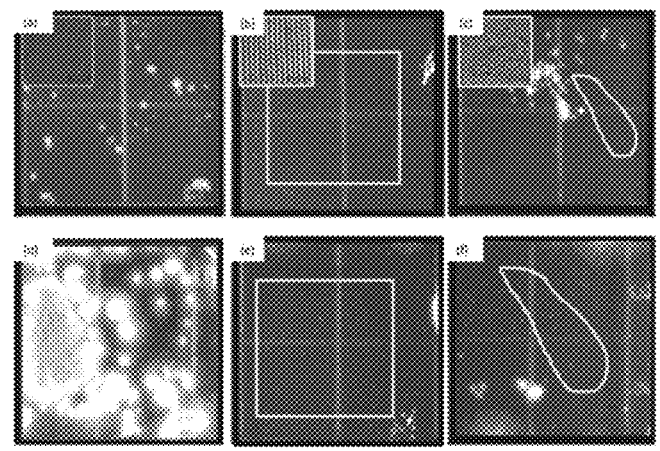

FIG. 4 illustrates, in accordance with embodiments herein, mold spores (top row=*Fusarium oxysporum*; bottom row=*Aspergillus fumigatus*) were incubated on PMMA surfaces—(a and d) flat, (b and e) 150 nm diameter pillars and (c and f) 100 nm diameter pillars. Each image area of the surfaces is 25×25 mm. The areas of the surface containing the nanopillared coating are indicated by light colored outlines. The results show that after incubation, viable mold spores survived on all surfaces areas except those coated by nanopillars. Insert: SEM images of nanopillars, scale bars are 1 µm.

DETAILED DESCRIPTION

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

The term "nanostructure(s)," as used herein, refers to structures which have a size between molecular and microscopic structures. Typically, such structures have at least one dimension on the nanoscale, e.g., between about 1 nm and about 999 nm. The nanostructures can be configured so as to include one or more of the following: (1) a nano surface having one dimension on the nanoscale, for example, a surface thickness between 1 nm and 999 nm; (2) a nanopillar or nanotube having two dimensions on the nanoscale, for example, a diameter and length each between 1 nm and 999 nm; and/or (3) a nanoparticle having three dimensions on the nanoscale, for example, the three spatial dimensions of the nanoparticle being between 1 nm and 999 nm. In one embodiment, the term nanopillar further refers to vertically oriented elongate structures, which may be straight, winding, zigzag, or crooked.

The term "microstructure(s)," as used herein, refers to structures which have at least one dimension on the microscale, e.g., between about 1 µm and about 999 µm. The microstructures can be configured so as to include one or more of the following: (1) a micro surface having one dimension on the microscale, for example, a surface thickness between 1 µm and 999 µm; (2) a micropillar or microtube having two dimensions on the microscale, for example, a diameter and length each between 1 µm and 999 µm; and/or (3) a microparticle having three dimensions on the microscale, for example, the three spatial dimensions of the nanoparticle being between 1 µm and 999 µm. In one embodiment, the term micropillar further refers to vertically oriented elongate structures, which may be straight, winding, zigzag, or crooked.

The term "lens," as used herein, refers to any ophthalmic device that resides in or on the eye. These devices may provide optical correction or may be cosmetic. For example, the term lens may refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the lenses are soft contact lenses are made from silicone elastomers or hydrogels, which include but are not limited to silicone hydrogels, and fluorohydrogels. In some embodiments, the lenses are curved.

As used herein, the term "BCL" refers to bandage contact lens.

As described herein, the inventors have developed a prophylactic BCL that 1) prevents microbial infections in an eye, 2) treats infection by dispensing antimicrobial medication at controlled rates for up to 10 days, and 3) is transparent. In accordance with various embodiments herein, this bandage may contain nanostructures, and provides a continuous treatment over 10 days and shields the eye from the environment, significantly diminishing the risk of infection while allowing damaged tissues to heal. In accordance with various embodiments herein, this device could also be used to aid patients in post-operative care. The transparency allows the patient to carry on his/her daily activities, for example. In another embodiment, the novelty of the dual-use design is that it functions both as a bacterial and fungal infection preventative and an ocular antimicrobial drug delivery treatment. As further described herein, in one embodiment, the bandage shields the eye from the environment and provides a continuous long-term treatment, thus significantly diminishing the risk of infection, and simultaneously allows damaged tissues to heal. It allows the user to maintain vision to the extent allowed by the nature of the injury.

In one embodiment, the present invention provides a device, comprising an antimicrobial bandage contact lens (BCL), wherein the antimicrobial BCL shields the eye from the environment while providing continuous long term treatment. In another embodiment, the antimicrobial BCL acts as a prophylactic device that prevents microbial infections in an eye using inherently antimicrobial biomaterials with nanotopography. In another embodiment, the antimicrobial BCL treats existing infection by dispensing antimicrobial medication at controlled rates over a period of up to 10 days. In another embodiment, the antimicrobial BCL is transparent. In another embodiment, the antimicrobial BCL diminishes the risk of infection while simultaneously allowing damaged tissues to heal. In another embodiment, the device allows the user to maintain vision to the extent allowed by the nature of the injury. In another embodiment, the antimicrobial BCL comprises a plurality of nanostructures fabricated on the surface.

In another embodiment, the BCL provides an affordable therapeutic device for both prevention and treatment of bacterial and fungal infections to the patient population affected by contact lens infection. For example, no existing device incorporates antimicrobial materials and textures, and can provide continuous long term drug elution for the prevention of microbial infection.

Figure 1:
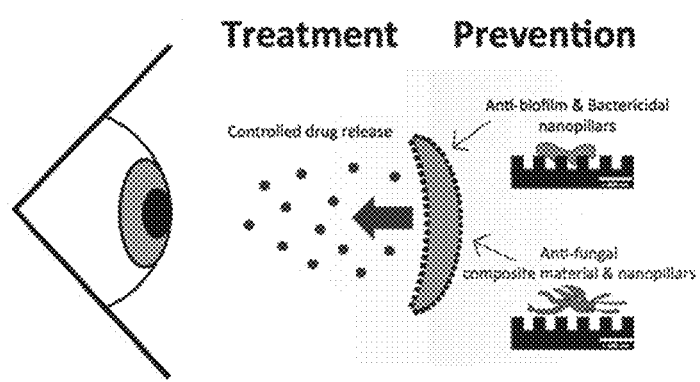
FIG. 1 illustrates, in accordance with embodiments herein, a schematic of BCL with (left) controlled drug release illustrating microbial infection treatment mechanism and (right) antibiofilm and antimicrobial nanopillars with inherently antimicrobial composite materials for infection prevention.

In another embodiment, the prophylactic and therapeutic device is a biocomposite, nanopatterned bandage contact lens (BCL). The antibacterial and antifungal surface is designed to be placed over the ocular lens to prevent ocular microbial infections while simultaneously delivering a drug at a controlled release rate that aids in healing of an injured or infected eye. As disclosed herein, the inventors have designed a transparent, therapeutic bandage material that harnesses advanced nanotechnology to combine (1) inherently antimicrobial bio-materials; (2) antimicrobial nano-architectures; and (3) an innovative biocomposite modality for antimicrobial drug delivery. A scheme of the bandage is shown in FIG. 1 herein.

In another embodiment, the innovative biocomposite is not necessary. For example, it could be used when there is no preexisting infection and/or is advantageous for preventing infection when the contact lens is used for up to 10 days.

Figure 2:
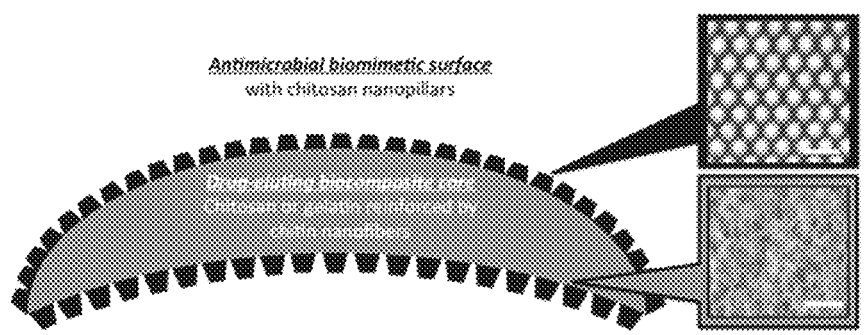
FIG. 2 illustrates, in accordance with embodiments herein, a schematic of the three-layer antifungal bandage. The surface layers are made of an inherently antifungal material (chitosan) and will be formed into the shape of antimicrobial nanopillars. These surface layers will protect the lens surface from microbial growth and contamination.

In another embodiment, the present invention provides an antifungal bandage design. In one embodiment, the architecture of the novel antifungal bandage device comprises three layers: a drug-eluting hydrogel-composite core layer sandwiched between two surface layers of lubricating hydrogel with antimicrobial nanopillars. The functions of the three layers are: (1) the central layer of hydrogel-chitin composite provides structural and shape stability and strength, and acts as a reservoir for the long-term release of the antifungal and antibacterial drugs; and (2) the outer layers provide for wearability and antimicrobial shielding. The architecture of these layers is depicted in FIG. 2 herein.

In another embodiment, the present invention provides a drug-eluting biocomposite core layer with mechanical reinforcement. As further disclosed herein, the inventors fabricated the core layer from a composite of chitosan or gelatin matrix, reinforced by chitin nanofibers for mechanical stability. The core layer is impregnated with antifungal and antibacterial drugs to provide a continuous, low constant rate of drug release.

In accordance with various embodiments herein, the ophthalmologic bandage must deliver antimicrobial drugs to the injured cornea. The current treatment for fungal keratitis involves hourly applications of topical agents such as natamycin that penetrate the posterior stroma to kill the hyphae. Eye drops account for 90% of all ophthalmic formulations, yet they are continually washed away by natural tears, leading to short temporal spikes in the effective dosage. In another embodiment, the device will deliver a zeroth-order release rate kinetics (constant rate with time) for sustained release over time to deter growth of microbes for at least 10 days. Or, for example, a mixture of drugs can also be co-formulated for simultaneous delivery with natamycin, such as voriconazole or erythromycin (a triazole antifungal agent or an antibacterial drug, respectively, both commonly used in ocular injection and eye drops).

In another embodiment, the core of the proposed sandwich structure must also provide structural integrity and strength. To achieve this, we utilize a composite material comprised of chitin nanofibers embedded in hydrogel matrices of (1) gelatin and (2) chitosan. Chitin, a naturally occurring polysaccharide, is known for its biocompatibility, robust mechanical properties, antifungal properties, and applications in wound healing and drug delivery. Chitosan, a de-acetylated form of chitin, possesses inherent biocompatibility, antimicrobial properties, and ability to store and deliver additional antimicrobial agents. The chitin nanofibers provide mechanical reinforcement to the chitosan or to gelatin without producing turbidity, resulting in optical transparency. The precise mechanical properties are tunable to achieve maximum strength and wearability. In another embodiment, the material properties could be modified for implementation into different types of bandages.

In another embodiment, the present invention provides an antimicrobial surface. For example, in one embodiment, the surface layer of the composite antifungal bandage material is composed of inherently antimicrobial chitosan, fabricated into antimicrobial nanoarchitectures. To kill any fungi and bacteria that adhere to the material surface, the surface will be forested with antimicrobial nanopillars. Such surfaces have been proven bactericidal. As described in FIGS. 3-4 herein, the inventors have developed antibacterial synthetic polymer nanopillar arrays and shown that the nanopillared synthetic surfaces to be strongly anti-fungal. Results on nanopillars imprinted on poly(methyl methacrylate) (PMMA) demonstrate clearly that in areas where there are nanopillars, no *Fusarium* or *Aspergillus* fungi grew on these surfaces over 72 hours. In another embodiment, no central core comprising a hydrogel matrix is required.

In another embodiment, the present invention provides a method of treating an eye condition in an individual, comprising providing an antimicrobial bandage contact lens (BCL), wherein the antimicrobial BCL shields the eye from the environment while providing continuous long term treatment, and treating the individual. In another embodiment, the eye condition is an eye infection.

In another embodiment, the present invention provides an eye lens, comprising an inner surface layer with an antimicrobial shielding, a core layer, and an outer surface layer. In another embodiment, the outer surface layer comprises antimicrobial shielding. In another embodiment, the core layer comprises a drug eluting hydrogel composite core layer.

The present disclosure is also directed to a kit for adding a micro-structure or nano-structure coating in devices, such as contact lens with ocular drug delivery. The kit is useful for practicing the inventive method of providing the device with antimicrobial and/or microbicidal properties. The kit is an assemblage of materials or components, including at least one of the inventive compositions. Thus, in some embodiments the kit contains a composition comprising one or more elastomeric molds, polymer solution, and holders, as described above.

The exact nature of the components configured in the inventive kit depends on its intended purpose. For example, some embodiments are configured for the purpose of providing microbicidal and antimicrobial properties in medical devices. In one embodiment, the kit is configured particularly for the purpose of providing a nanostructure coating in touch devices. In another embodiment, the kit is configured for the purposes of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to provide microstructures or nanostructures on devices. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in the medical device industry and/or in the polymer industry. As used herein, the term "package" refers to a suitable solid matrix or material such as glass, plastic, paper, foil, and the like, capable of holding the individual kit components. Thus, for example, a package can be a glass vial used to contain suitable quantities of the presently disclosed inventive composition. The packaging material generally has an external label which indicates the contents and/or purpose of the kit and/or its components.

The method described herein is uniquely able to apply precisely defined (by the arbitrary, planar master mold) nano- or micro-structures to a variety of biomedical device materials on complex curved topographies.

Embodiments of the present disclosure are further described in the following examples. The examples are merely illustrative and do not in any way limit the scope of the invention as claimed.

EXAMPLES

Example 1

Anti Microbial Bandage Contact Lens with Ocular Drug Delivery

The novel device is an antimicrobial bandage contact lens (BCL) that 1) acts as a prophylactic device that prevents microbial infections in an eye using inherently antimicrobial biomaterials with nanotopography, 2) treats existing infection by dispensing antimicrobial medication at controlled rates over a period of up to 10 days, and 3) is transparent. This bandage shields the eye from the environment and provides a continuous long-term treatment, thus significantly diminishing the risk of infection, and simultaneously allows damaged tissues to heal. It allows the user to maintain vision to the extent allowed by the nature of the injury.

In one embodiment, the BCL will provide an affordable therapeutic device for both prevention and treatment of bacterial and fungal infections to the patient population affected by contact lens infection. No existing device incorporates antimicrobial materials and textures, and can provide continuous long term drug elution for the prevention of microbial infection.

In another embodiment, the prophylactic and therapeutic device is a biocomposite, nanopatterned bandage contact lens (BCL). The antibacterial and antifungal surface is designed to be placed over the ocular lens to prevent ocular microbial infections while simultaneously delivering a drug at a controlled release rate that aids in healing of an injured or infected eye. In accordance with embodiments herein, the inventors have designed a transparent, therapeutic bandage material that harnesses advanced nanotechnology to combine (1) inherently antimicrobial bio-materials; (2) antimicrobial nanoarchitectures; and (3) an innovative biocomposite modality for antimicrobial drug delivery. A scheme of the bandage is shown in FIG. 1 herein.

In another embodiment, the present invention provides an antifungal bandage design. In one embodiment, the architecture of the novel antifungal bandage device comprises three layers: a drug-eluting hydrogel-composite core layer sandwiched between two surface layers of lubricating hydrogel with antimicrobial nanopillars. The functions of the three layers are: (1) the central layer of hydrogel-chitin composite provides structural and shape stability and strength, and acts as a reservoir for the long-term release of the antifungal and antibacterial drugs; and (2) the outer layers provide for wearability and antimicrobial shielding. The architecture of these layers is depicted in FIG. 2 herein.

In another embodiment, the present invention provides a drug-eluting biocomposite core layer with mechanical reinforcement. As further disclosed herein, the inventors fabricated the core layer from a composite of chitosan or gelatin matrix, reinforced by chitin nanofibers for mechanical stability. The core layer is impregnated with antifungal and antibacterial drugs to provide a continuous, low constant rate of drug release.

In accordance with various embodiments herein, the ophthalmologic bandage must deliver antimicrobial drugs to the injured cornea. The current treatment for fungal keratitis involves hourly applications of topical agents such as natamycin that penetrate the posterior stroma to kill the hyphae. Eye drops account for 90% of all ophthalmic formulations, yet they are continually washed away by natural tears, leading to short temporal spikes in the effective dosage. In another embodiment, the device will deliver a zeroth-order release rate kinetics (constant rate with time) for sustained release over time to deter growth of microbes for at least 10 days. Or, for example, a mixture of drugs can also be co-formulated for simultaneous delivery with natamycin, such as voriconazole or erythromycin (a triazole antifungal agent or an antibacterial drug, respectively, both commonly used in ocular injection and eye drops).

In another embodiment, the core of the proposed sandwich structure must also provide structural integrity and strength. To achieve this, we utilize a composite material comprised of chitin nanofibers embedded in hydrogel matrices of (1) gelatin and (2) chitosan. Chitin, a naturally occurring polysaccharide, is known for its biocompatibility, robust mechanical properties, antifungal properties, and applications in wound healing and drug delivery. Chitosan, a de-acetylated form of chitin, possesses inherent biocompatibility, antimicrobial properties, and ability to store and deliver additional antimicrobial agents. The chitin nanofibers provide mechanical reinforcement to the chitosan or to gelatin without producing turbidity, resulting in optical transparency. The precise mechanical properties are tunable to achieve maximum strength and wearability. In another embodiment, the material properties could be modified for implementation into different types of bandages.

In another embodiment, the present invention provides an antimicrobial surface. For example, in one embodiment, the surface layer of the composite antifungal bandage material is composed of inherently antimicrobial chitosan, fabricated into antimicrobial nanoarchitectures. To kill any fungi and bacteria that adhere to the material surface, the surface will be forested with antimicrobial nanopillars. Such surfaces have been proven bactericidal. As described in FIGS. 3-4 herein, the inventors have developed antibacterial synthetic polymer nanopillar arrays and shown that the nanopillared synthetic surfaces to be strongly anti-fungal. Results on nanopillars imprinted on poly(methyl methacrylate) (PMMA) demonstrate clearly that in areas where there are nanopillars, no *Fusarium* or *Aspergillus* fungi grew on these surfaces over 72 hours.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A bandage contact lens, comprising:
   a first and a second layers, the first and the second layers each having an inner surface and an outer surface and each comprising an array of nanopillars characterized by antimicrobial properties disposed on at least the outer surface; and
   a void space enclosed by the inner surfaces of the first and the second layers.

2. The bandage contact lens of claim 1, wherein the first and the second layers comprise an inherently antimicrobial material.

3. The bandage contact lens of claim 1, wherein the array of nanopillars is characterized by a nanopillar diameter, a nanopillar periodicity, and a nanopillar height.

4. The bandage contact lens of claim 2, wherein the inherently antimicrobial material comprises chitosan.

5. The bandage contact lens of claim 3, wherein the nanopillar diameter is at least 100 nm.

6. The bandage contact lens of claim 1, wherein the void space is filled with a transparent material that elutes at least one drug.

7. The bandage contact lens of claim 1, wherein the void space is filled with a composite material comprising a hydrogel matrix reinforced with nanofibers.

8. The bandage contact lens of claim 6, wherein the at least one drug is eluted continuously.

9. The bandage contact lens of claim 6, wherein the at least one drug is selected from the group consisting of:
   natamycin, voriconazole, and erythromycin.

10. The bandage contact lens of claim 1, wherein the bandage contact lens is transparent.

11. The bandage contact lens of claim 7, wherein the hydrogel matrix comprises a material selected from the group consisting of:
    chitosan, gelatin, and any combination thereof.

12. The bandage contact lens of claim 7, wherein the nanofibers comprise chitin nanofibers.

13. The bandage contact lens of claim 7, wherein the composite material provides strength, stability, and shape for the bandage contact lens.

14. The bandage contact lens of claim 1, wherein the first and the second layers comprise a lubricating hydrogel.

15. The bandage contact lens of claim 1, wherein the first and the second layers comprise a transparent, flexible and or soft material suitable for fabrication of eye contact lenses.

16. The bandage contact lens of claim 7, wherein the bandage contact lens is transparent.

17. The bandage contact lens of claim 1, wherein the first and the second layers comprise poly(methyl methacrylate.

18. A device, comprising an antimicrobial bandage contact lens comprising:
    a first and a second layers, the first and the second layers each having an inner surface and an outer surface and each comprising an array of nanopillars characterized by antimicrobial properties disposed on at least the outer surface; and
    a void space enclosed by the inner surfaces of the first and the second layers;
    wherein the antimicrobial bandage contact lens shields an eye afflicted by a medical condition from an environment during a treatment of the medical condition.

19. The device of claim 18, wherein the first and the second layers comprise an inherently antimicrobial material, and the antimicrobial bandage contact lens acts as a prophylactic device that prevents microbial infections in the eye.

20. The device of claim 18, wherein the void space is filled with a transparent material that elutes at least one drug at a controlled rate over a period of up to 10 days or longer.

21. The device of claim 18, wherein the antimicrobial bandage contact lens is transparent.

22. The device of claim 18, wherein the void space is filled with a transparent composite material comprising a hydrogel matrix reinforced with nanofibers, and wherein the transparent composite material provides strength, stability, and shape for the antimicrobial bandage contact lens.

23. The device of claim 18, wherein the first and the second layers comprise a transparent, flexible and or soft material suitable for fabrication of eye contact lenses.

24. The device of claim 18, wherein the array of nanopillars is characterized by a nanopillar diameter of at least 100 nm.

* * * * *

UNITED STATES PATENT AND TRADEMARK OFFICE
CERTIFICATE OF CORRECTION

| | | |
|---|---|---|
| PATENT NO. | : 11,086,049 B2 | Page 1 of 1 |
| APPLICATION NO. | : 16/150976 | |
| DATED | : August 10, 2021 | |
| INVENTOR(S) | : Albert Yee et al. | |

It is certified that error appears in the above-identified patent and that said Letters Patent is hereby corrected as shown below:

In the Specification

Column 1, Line 11 The Statement of Federal Funding should read:
STATEMENT OF FEDERALLY SPONSORED RESEARCH
This invention was made with government support under Grant No. W81XWH-17-1-0355 awarded by the U.S. Department of Defense. The government has certain rights in the invention.

Signed and Sealed this
Nineteenth Day of September, 2023

*Katherine Kelly Vidal*

Katherine Kelly Vidal
*Director of the United States Patent and Trademark Office*